United States Patent [19]

Nienburg et al.

[11] 3,959,385

[45] May 25, 1976

[54] PRODUCTION OF ALCOHOLS AND/OR ALDEHYDES

[75] Inventors: Hans Juergen Nienburg, Ludwigshafen; Wilhelm Kniese, Limburgerhof; Rudolf Kummer, Frankenthal; Peter Tavs, Limburgerhof, all of Germany

[73] Assignee: Badische Anilin- & Soda-Fabrik Aktiengesellschaft, Ludwigshafen (Rhine), Germany

[22] Filed: Oct. 15, 1970

[21] Appl. No.: 81,168

[30] Foreign Application Priority Data

Nov. 6, 1969 Germany............................ 1955828

[52] U.S. Cl. .................. 260/604 HF; 260/638 HF
[51] Int. Cl.$^2$......................................... C07C 45/08
[58] Field of Search ............... 260/604 HF, 638 HF, 260/598, 599

[56] References Cited
UNITED STATES PATENTS

| | | | |
|---|---|---|---|
| 3,239,569 | 3/1966 | Slaugh et al. ................. | 260/604 HF |
| 3,274,263 | 9/1966 | Greene et al. ................ | 260/604 HF |
| 3,400,163 | 9/1968 | Mason et al. ................. | 260/604 HF |
| 3,646,079 | 2/1972 | Lawrenson .................... | 260/604 HF |
| 3,681,465 | 8/1972 | Falbe et al. ................... | 260/604 HF |

FOREIGN PATENTS OR APPLICATIONS 1,206,063   9/1970   United Kingdom................ 260/604

*Primary Examiner*—James O. Thomas, Jr.
*Assistant Examiner*—W. B. Lone
*Attorney, Agent, or Firm*—Johnston, Keil, Thompson & Shurtleff

[57] ABSTRACT

An improved process for the production of aldehydes and alcohols by the oxo process comprising the reaction of olefinically unsaturated compounds with carbon monoxide and hydrogen at elevated temperatures and elevated pressures in the presence of carbonyl complexes of metals in Group VIII of the Periodic Table modified by trisubstituted organic phosphines and in the presence of alkali or alkaline earth metal salts of carboxylic acids, the improvement comprising the use of modifying agents which consist of trisubstituted organic phosphines containing one or more carboxylic acid groups, at least one of which is present in the form of its alkali metal or alkaline earth metal salt.

9 Claims, No Drawings

PRODUCTION OF ALCOHOLS AND/OR ALDEHYDES

The invention relates to an improved process for the production of aldehydes and/or alcohols by the oxo process comprising the reaction of olefinically unsaturated compounds with carbon monoxide and hydrogen in the presence of carbonyl complexes of metals in Group VIII of the Periodic Table modified by trisubstituted organic phosphines.

In industry, a widely use process for the production of aldehydes and alcohols is the oxo reaction, in which olefinically unsaturated compounds, particularly olefins, are reacted with carbon monoxide and hydrogen in the presence of carbonyl compounds as catalysts. The process suffers from the drawbacks that is produces a certain amount of branched aldehydes and alcohols, and these are less desirable. Another disadvantage of this process is that the carbonyl complexes used dissociate readily and thus produce deposits of catalyst metal in the equipment. A number of processes are also known in which a larger proportion of straight-chained aldehydes and alcohols is obtained. Thus the published documents of Dutch Patent Application 64.00701 and German Published Application DAS, 1,186,455 describe the use in the oxo process of carbonyls of metals in Group VIII of the Periodic Table which are modified by trisubstituted organic phosphines to produce substantially straight-chained oxo reaction products. The trisubstituted organic phosphines which are used as modifying agents have the disadvantage, however, that their activity falls rapidly and also, they are difficult to separate, because the phosphines appear in the desired products as impurities when the oxo reaction mixture has been worked up by distillation, and this is undesirable. As described in German Published Application DAS 1,212,953, the life of the organic phosphines used as modifying agents is improved by carrying out oxo reactions in the presence of carboxylic acids or their alkali or alkaline earth metal salts. However, this process has the drawbacks that the catalysts used still fail to comply with the stability requirements demanded in industry and also the volatility of the organic phosphines used as modifying agents is not diminished and consequently these compounds are still present in the desired products as impurities after working up.

It is an object of the invention to provide a process in which higher proportions of straight-chained compounds are obtained.

It is a further object of the invention to provide a process in which the catalysts used show a high degree of stability and are readily isolated, so that it is almost impossible for impurities to appear in the desired final products.

In accordance with the present invention these and other objects and advantages are achieved in an improved process for the production of aldehydes and alcohols by the oxo process comprising the reaction of olefinically unsaturated compounds with carbon monoxide and hydrogen at elevated temperatures and increased pressures in the presence or carbonyl complexes of metals in Group VIII of the Periodic Table modified by trisubstituted organic phosphines and in the presence of alkali or alkaline earth metal salts of carboxylic acids, the improvement comprising the use of modifying agents which consists of trisubstituted organic phosphines containing one or more carboxylic acid groups, at least one of which is present in the form of its alkali or alkaline earth metal salt.

We prefer to use aliphatic, cycloaliphatic or araliphatic olefinically unsaturated compounds of up to 20 carbon atoms, in particular of up to 16 carbon atoms. The preferred olefinically unsaturated compounds may contain a number of double bonds, for example two nonconjugated double bonds or substituents which are inert under the conditions of the reaction, such as alkoxy of from 1 to 4 carbon atoms, carboxyl, carbalkoxy of from 2 to 9 carbon atoms, acyloxy derived from fatty acids, cycloalkane carboxylic acids or aromatic acids of up to 16 carbon atoms, or hydroxyl. THe particularly preferred starting materials are olefinically unsaturated compounds of hydrocarbon structure. Of particular commercial interest are olefins of from 2 to 20, especially of from 2 to 16, carbon atoms, in particular those having terminal double bonds. Suitable olefinically unsaturated compounds are, for example, ethylene, propylene, hexene-1, octene-1, decene-1, cyclohexene, styrene, propenylbenzene, allyl alcohol, allyl methyl ether, methyl crotonate, methyl acrylate, olefin mixtures such as are from the oligomerization of propene and butene, such as so-called trimeric propylene or codibutylene and butene-3,4-diol-1,2-diacetate.

Carbon monoxide and hydrogen are generally used in proportions by volume of from 1:1 to 1:10, in particular from 1:1 to 1:3.

The olefinically unsaturated compounds may be used in stoichiometric amounts based on the mixture of carbon monoxide and hydrogen, but it is advantageous to use the said gas mixture in excess of the stoichiometric amount. It is even possible to use considerably more than the stoichiometric excess, for example up to 500% excess.

The reaction is advantageously carried out at temperatures rangingg from 140° to 250°C. Particularly good results are obtained when temperatures of from 190° to 230°C are used. Good results are obtained when the reaction is carried out under pressures of from, say, 20 to 350 atmospheres. It is advantageous to use pressures of from 30 to 80 atmospheres.

It is possible to carry out the reaction without the use of additional solvents, in which case the olefinically unsaturated compounds used as starting materials act as solvents.

However, the reaction is generally carried out in the presence of solvents which are inert under the conditions of the reaction, for example hydrocarbons such as cyclohexane or xylene, and alcohols such as butanol or aldehydes such as butyraldehyde. In commercial operation it is convenient to use the products of the reaction as solvents.

The reaction is carried out in the presence of carbonyl complexes of metals in Group VIII of the Periodic Table, which are modified by trisubstituted organic phosphines containing one or more carboxylic acid groups, at least one of which is in the form of its alkali or alkaline earth metal salt. Preferred carbonyl complexes of metals in Group VIII of the Periodic Table are those of cobalt or rhodium. Cobalt carbonyl complexes have been found to be particularly useful commercially. Preferred catalysts contain metal and phosphorus in an atomic ratio of from 1:1 to 1:4, in particular from 1:1 to 1:2.

The tertiary organic phosphines used as modifying agents generally have the same or different aliphatic, cycloaliphatic, araliphatic or aromatic radicals, of which at least one contains a carboxylic group. It is possible, however, for a number of carboxyl groups, say up to 4 carboxyl groups, to be present in the tertiary phosphine molecule. It is further possible for the phosphorus atom to form part of a heterocyclic ring, for example a 5 or 6 membered heterocyclic ring, and for the heterocyclic ring or the third substituted to contain one or more carboxyl groups. Preferred tertiary organic phosphines have same or different aliphatic radicals of up to 20 carbon atoms, cycloaliphatic radicals of from 5 to 12 carbon atoms, araliphatic radicals of from 7 to 14 carbon atoms, or aromatic radicals of from 6 to 12 carbon atoms. The most preferred tertiary phosphines are those in which the radicals containg said number of carbon atoms have, apart from the carboxyl groups or groups contained therein, hydrocarbon structure. Of particular commercial interest are modifying agents consisting of tertiary organic phosphines of the general formula $$R_p-P[(CH_2)_m COOMe]_n$$

where

R stands for alkyl of from 1 to 25 carbon atoms, cyclohexyl, phenyl, benzyl or, preferably, methyl, Me stands for an alkali or alkaline earth cation, in particular sodium or potassium, in at least a stoichiometric amount for a carboxyl group, m stands for an integer of from 1 to 14 inclusive, in particular from 8 to 14, n stands for 1 to 3 inclusive, in particular for 1, and p stands for 3-n, in particular for 2.

Suitable tertiary organic phosphines are, for example, bis-2-carboxyethyldodecyl phosphine, bis-2-carboxyethylphenyl phosphine, 2-carboxyethyldiphenyl phosphine, 10-carboxydecyldimethyl phosphine, 9(10'-carboxydecyl)-9-phosphabicyclo(4,2,1)-nonane, 9-(10'-carboxydecyl)-9-phosphabicyclo(3,3,1)-nonane, 9-n-dodecyl-9-phosphabicyclo(4,2,1)-nonane-3,4,7,8-tetracarboxylic acid, 9-n-dodecyl-9-phosphabicyclo-(3,3,1)-nonane-2,3,6,7-tetracarboxylic acid, 9-n-octyl-9-phosphabicyclo(4,2,1)-nonane-3,4,7,8-tetracarboxylic acid, and 9-n-octyl-9-phosphabicyclo(3,3,1)-nonane-2,3,6,7-tetracarboxylic acid.

We prefer to use from 0.1 to 2% by weight of the said catalysts, calculated as catalyst metal based on the amount olefinically unsaturated compounds used. We have found amounts ranging from 0.2 to 1% by weight to be particularly convenient. It is possible to use preformed catalysts in the oxo reaction or alternatively, the starting materials for the catalysts may be added to the reaction separately or as partly preformed components. For example the esters of the phosphinic carboxylic acids or the free carboxylic acids themselves may be included in the reaction mixture and then converted to the desired salt in the reaction zone by the addition of the stoichiometric amount of alkali solution. The catalyst then forms automatically under the conditions of the reaction.

The process of the invention is carried out, for example, by passing olefins, a mixture of carbon monoxide and hydrogen and catalyst of the stated composition, optionally together with a suitable solvent, to the bottom of a vertical high-pressure tube in the desired proportions, and effecting the reaction under the stated conditions of temperature and pressure.

After the pressure has been released the reaction mixture is separated from the non-volatile and thermally stable catalyst by distillation, the catalyst remaining in the liquor at the bottom of the tube to be re-used as catalyst.

The aldehydes and alcohols produced by the process of the invention are valuable for the production of solvents and plasticizers for polymers and also in the production of detergents.

In the following Examples the parts given are by weight unless otherwise stated. The parts by weight relate to the parts by volume as the kilogram to the liter.

EXAMPLE 1

A high-pressure vessel of a capacity of 1,700 parts by volume is charged with 100 parts of butanol and 100 parts of octene, a mixture of carbon monoxide and hydrogen in the proportions of 1:1 by volume then being introduced under pressure. The content of the tube are then heated to 180°C until a final pressure of 80 atmospheres gauge is reached. There are then added, through a pressure lock, 5.1 parts of cobalt ethylhexanoate, dissolved in 46 parts of octene, together with 8.4 parts of the potassium salt of 10-carboxyldecyldimethyl phosphine, dissolved in 46 parts of butanol. The pressure during the reaction is maintained at 80 atmospheres gauge by continuously introducing fresh gas mixture under pressure. After 2 hours samples are taken and examined by gas chromatography. 25.2% of the octene introduced is unchanged. The mixture also contains 2.7% of octane, 6.9% of isononanol, 53% of n-nonanol, 2.7% of iso-nonanol and 9.6% of n-nonanol (based on the sum of the $C_8$ and $C_9$ products). The total amount of straight-chained products is 78%.

EXAMPLE 2

Example 1 is repeated except that 9.2 parts of 10-carboxydecyldiethyl phosphine in the form of its potassium salt are used. After the reaction has proceeded for 2 hours, 39.5% of the octene is still unconverted. The mixture also contains 4.0% of octane, 4.2% of isononanol, 36.6% of n-nonanol, 3.3% of iso-nonanal and 12.4% of n-nonanal. The content of normal compounds is 87%.

EXAMPLE 3

Example 1 is repeated except that 11.8 parts of β-carboxyethylβ-carbethoxyethyldodecyl phosphine are used in the form of the potassium salt. After the reaction has proceeded for 2 hours, 38.9% of the octene is still unconverted. The mixture also contains 4.2% of octane, 6.1% of iso-nonanol, 35.4% of n-nonanol, 3.3% of iso-nonanal and 12.0% of n-nonanal. The content of normal compounds is 83%.

The excellent properties of the catalysts of the invention are demonstrated in the following comparative Examples.

EXAMPLES 4 to 6

To the bottom of a high-pressure vessel of a capacity of 500 parts by volume there are passed, per hour, 80 cm³ of octene-1, in which 0.3% of cobalt in the form of its 2-ethylhexanoate are dissolved, and from 12 to 13 cm³ of methanol, in which sufficient phosphine is dissolved to make the ratio of cobalt to phosphorus equal to 1:2. The reaction is carried out at a pressure of 80 atmospheres gauge provided by a gas mixture of carbon monoxide and hydrogen in the proportions of 1:2 by volume and at a temperature of 230°C. The residence time is 2.5 hours. The type of phosphine used, the degree of conversion of the octene and the amount of non-decomposed catalyst may be seen from the following Table.

Table

| Example | Phosphine | Unreacted octene (%) | Conc. of Co in reaction product |
| --- | --- | --- | --- |
| 4 (Comp.Ex.) | tris-n-butyl phosphine | 11.5 | 0.05 |
| 5 | sodium salt of 10-carboxydecyldiethyl phosphine | 8.7 | 0.21 |
| 6 | sodium salt of 10-carboxydecyldimethyl phosphine | 6.4 | 0.21 |

We claim:

1. An improved process for the production of aldehydes and alcohols by the oxo process comprising reacting an aliphatic, cycloaliphatic or araliphatic olefinically unsaturated compound of up to 20 carbon atoms with carbon monoxide and hydrogen at a temperature of from 140° to 250°C and at a pressure of from 20 to 350 atmospheres in the presence of carbonyl complexes of metals in Group VIII of the Periodic Table modified by trisubstituted organic phosphines and in the presence of alkali or alkaline earth metal salts of carboxylic acids, the improvement which comprises using as the trisubstituted organic phosphine modifying agent a trisubstituted organic phosphine having the structural formula

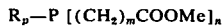

$$R_p-P\,[(CH_2)_m COOMe]_n$$

where R stands for methyl or ethyl, Me stands for potassium or sodium in at least a stoichiometric amount for a carboxyl group, $m$ stands for an integer of from 8 to 14 inclusive, $n$ stands for 1 to 3 inclusive, and $p$ stands for $3-n$.

2. A process as claimed in claim 1, said trisubstituted organic phosphine being 10-carboxydecyldiethyl phosphine in the form of its potassium or sodium salt.

3. A process as claimed in claim 1, said trisubstituted organic phosphine being 10-carboxyldecyldimethyl phosphine in the form of its potassium or sodium salt.

4. A process as claimed in claim 1 wherein straight-chained olefins of from 2 to 16 carbon atoms and having one terminal double bond are used as starting material.

5. A process as claimed in claim 1, wherein a temperature of from 190° to 230°C is used.

6. A process as claimed in claim 1 wherein a pressure of from 30 to 80 atmospheres is used.

7. A process as claimed in claim 1 wherein cobalt carbonyl complexes are used.

8. A process as claimed in claim 1 wherein the atomic ratio of catalyst metal to phosphorus is from 1:1 to 1:4.

9. A process as claimed in claim 1 wherein R is methyl, $p$ is 2, and $n$ is 1.

* * * * *